United States Patent [19]

Braden et al.

[11] 4,146,795

[45] Mar. 27, 1979

[54] FLEXIBLE CABLE CONTROL AND TAKE-UP MECHANISM

[75] Inventors: Arthur B. Braden, Mentor; Joseph J. Lekan, Willoughby Hills; Samual K. Taylor, Chardon; Joseph B. Richey, Shaker Heights, all of Ohio

[73] Assignee: Ohio-Nuclear, Inc., Solon, Ohio

[21] Appl. No.: 849,179

[22] Filed: Nov. 7, 1977

Related U.S. Application Data

[63] Continuation of Ser. No. 700,174, Jun. 28, 1976, abandoned.

[51] Int. Cl.$^2$ .............................................. G03B 41/16
[52] U.S. Cl. ................................ 250/445 T; 250/523
[58] Field of Search ................ 250/439 R, 444, 445 R, 250/445 T, 446, 447, 448, 449, 450, 490, 522, 523, 524, 525, 401, 402

[56] References Cited

U.S. PATENT DOCUMENTS

| 3,541,334 | 11/1970 | Sobolewski | 250/523 |
| 4,001,593 | 1/1977 | Wing | 250/445 T |

*Primary Examiner*—Craig E. Church
*Attorney, Agent, or Firm*—Fay & Sharpe

[57] ABSTRACT

A control and take-up mechanism for controlling and protecting at least one elongated cable and the like which may be employed to supply operating power, fluids, controls and so on to an operating member mounted within an apparatus and wherein the operating member is selectively movable within the apparatus through an operating plane between a first position and a second position spaced therefrom. The take-up mechanism is comprised of an arcuate cable trough fixedly mounted to the apparatus in a plane parallel to the operating plane with a portion of the elongated cable leading to the operating member longitudinally disposed therein. A cable wheel assembly is received in the trough in rolling engagement therewith and includes a hub and opposed sides which define a cable channel therebetween. The cable wheel assembly is constructed so that the sides and hub are rotatable about the assembly axis independently of each other in order to eliminate undesired sliding of the cable in the trough and/or around the hub during pay out of the cable in response to movement of the operating member between the first and second positions. The cable extends from its source through the trough, around a portion of the cable wheel assembly hub and then to the operating member itself. When the operating member is in the first position, the cable wheel assembly is disposed adjacent one end of the cable trough and as the operating member is moved toward the second position, the cable wheel assembly is pulled by the cable tension along the trough toward the other end thereof. Biasing means communicate with the cable wheel assembly to continuously urge the assembly toward one end of the cable trough against the tension of the cable. Means are also provided for maintaining the cable in substantially the same degree of contact with the wheel assembly hub as the cable moves therearound when the operating member is moved between the first and second positions.

27 Claims, 9 Drawing Figures

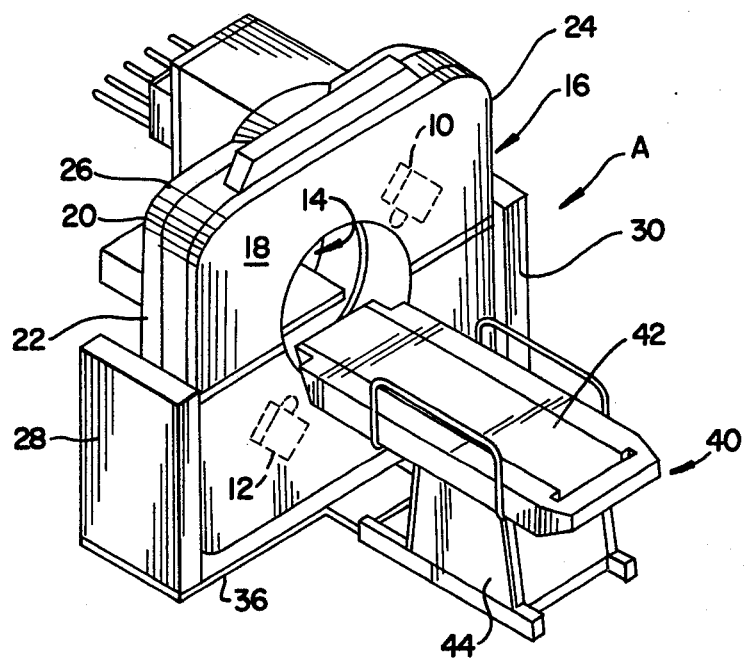
FIG. 1
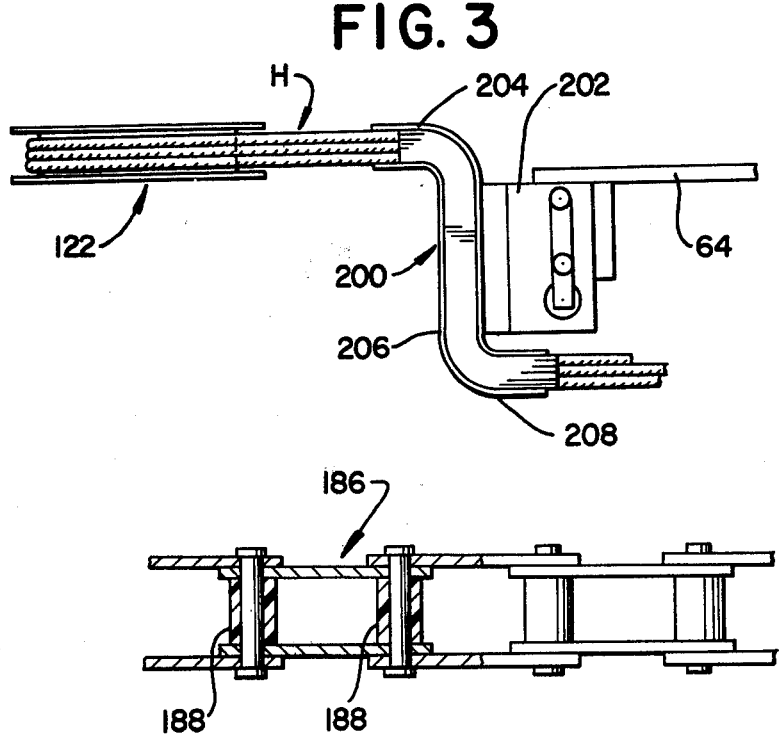
FIG. 3
FIG. 7

FLEXIBLE CABLE CONTROL AND TAKE-UP MECHANISM

This is a continuation of application Ser. No. 700,174, filed June 28, 1976, now abandoned.

BACKGROUND OF THE INVENTION

This invention pertains to the art of control and take-up mechanisms and more particularly to a cable control and take-up mechanism for elongated flexible cables.

The invention is particularly applicable to a cable control and take-up mechanism for use in X-ray scanner apparatus where a number of individual cables which comprise a cable harness are employed to supply high power, fluid, electronics and the like to X-ray scanner components mounted in a frame and which components are selectively movable between a number of different positions for performing X-raying functions and will be described with particular reference thereto. However, it will be appreciated by those skilled in the art that the invention has broader applications and may be used in other types of apparatus and environments where it is desired to maintain control and take-up of at least one elongated flexible cable-like member which is movable in an apparatus between a number of different positions and wherein the cable could otherwise become entangled in the apparatus or be unnecessarily prematurely worn requiring replacement.

The subject cable control and take-up mechanism is particularly applicable to use on X-ray diagnostic medical instrumentation commonly known as a traverse, axial, computerized tomographic X-ray scanner. The general techniques employed in such instrumentation are disclosed in detail in the prior Hounsfield U.S. Pat. No. 3,778,614, the disclosure of which is incorporated herein by reference, and the general overall operation of such apparatus is generally shown in the commonly assigned pending patent application Ser. No. 691,313, filed June 1, 1976.

In such apparatus, a radiation source and a radiation detector are mounted in a spaced apart relationship from each other in a framework on opposite sides of an enlarged patient opening. The patient may be variously located in the opening and then X-rayed by means of the radiation source and detector in conjunction with attendant controls, processing equipment and display terminals. In order that a full and complete patient X-ray may be taken, the radiation source and detector are desirably movable about the patient opening in the scanner framework thus permitting X-rays to be taken at various angles and elevations through the patient. Accordingly, means are provided for selectively and simultaneously moving the radiation source and detector components about the patient opening to a number of different positions.

While sometimes only relative rotational movement of the source and detector may be provided around the patient opening, it has been found particularly desirable to provide both rotational and traversing movement to facilitate the performance of a more versatile and complete X-raying operation. For this purpose and in some instances, the scanner frame includes a generally vertically disposed rotate frame which is selectively rotatable about the axis of the patient opening. Mounted to this rotate frame is a traverse frame which is independently movable across the rotate frame. The radiation source and radiation detector are mounted on opposite sides of the traverse frame in order that they may be selectively and simultaneously either rotated and/or traversed to predetermined positions or through a predetermined path to obtain the desired pattern of patient X-rays.

In order to render the radiation source and detector operative in the general manner heretofore described through the sophisticated X-ray scanner apparatus and attendant controls, processing equipment and display terminals, it is necessary that a number of flexible cables which comprise a cable harness be strung from this attendant equipment, through the X-ray scanner apparatus and to the radiation source and detector themselves. The sensitivity of the type of process and apparatus involved requires that these cables also have a certain thickness of insulation to protect them from inadvertent damage during apparatus operation. Because these cables are strung through the X-ray scanner apparatus to the radiation source and detector, and because the radiation source and detector are selectively movable during the scanner apparatus operation, a certain amount of slack must be provided in the cables between the areas at which they enter the apparatus and the area at which they are connected to the radiation source and detector. This, of course, allows these components to be moved unimpeded by the cables between their various operative positions.

Typically, the X-ray scanner frame is extremely crowded with a substantial number of individual components so that there is only a very limited and close spaced area in which to thread the cables from the entrance to the X-ray scanner apparatus to the radiation source and detector and to also provide the necessary slack required to facilitate movement of these components. Moreover, care must be taken in threading and locating the cables so that during actual operation of the scanner and movement of the radiation source and detector between their various positions to secure the necessary patient X-rays, the cables do not rub or otherwise engage the apparatus in a manner causing destruction or irreparable damage to them.

The present invention contemplates a new and improved apparatus which overcomes the above referred to problems and others and provides a cable control and take-up mechanism which is simple in design, operation and economical. It also positively controls and guides a plurality of flexible cables extending between a stationary mounted area and a movable operating member and which may be adapted to use in a number of different apparatus in a number of different environments where cable control and take-up mechanisms may be advantageously employed.

BRIEF DESCRIPTION OF THE INVENTION

In accordance with the present invention, there is provided a cable control and take-up mechanism for at least one elongated flexible cable and the like which is stationarily mounted at a first area in an apparatus and extends to a movable second area in the apparatus for operable connection to an operating member. The operating member itself is selectively movable relative to the apparatus through predetermined paths from a first position to a plurality of second positions spaced from the first position. The control and take-up mechanism comprises a cable track fixedly mounted to the apparatus and which has first and second spaced apart ends with a portion of the cable extending between the first and second areas passing longitudinally through a portion of the track. A cable wheel assembly communicates with the track and is adapted for selective movement relative thereto between the track first and second ends with a portion of the cable received around the wheel assembly between the track and the second area. The wheel assembly is selectively movable relative to the track between a home position adjacent the track first end and an extended position spaced along the track toward the track second end in response to the tension of the at least one cable as the operating member is moved between the first and second positions. The mechanism further includes means for continuously urging the cable wheel assembly toward the home position against the tension of the cable.

In accordance with another aspect of the present invention, the cable wheel is comprised of a cylindrical hub having generally circular sides extending radially outward therefrom adjacent the ends thereof. The assembly sides are rotatable about the assembly axis independently of the hub and the outer peripheral edges of the sides are disposed in rolling engagement with the track.

In accordance with another aspect of the present invention, the means for continuously urging comprises a spring biased reel spaced remote from the cable wheel assembly and operably connected thereto by an elongated flexible member. The reel is spring biased in a manner such that the cable wheel assembly will be continuously urged toward the home position with the elongated flexible member being paid off of and onto the reel as the wheel assembly is moved between the home and extended positions responsive to movement of the operating member.

In accordance with yet a further aspect of the present invention, means are included for maintaining the cable in contact with the wheel assembly hub over the same degree of the circumference thereof as the cable wheel assembly is moved between the home and extended positions in response to movement of the operating member.

One advantage to the present invention is that it assures controlled behavior of the flexible cables which comprise the cable harness for an X-ray scanner apparatus, that is, high power cables, oil hoses and electronic cables, within the confines of the X-ray scanner gantry frame.

Another advantage to the subject invention is that the cable control and take-up mechanism is of a compact design so that it requires a minimum of space within the X-ray scanner gantry frame.

Still another advantage of the present invention is the provision of a cable control and take-up mechanism which aids in protecting the cables to increase their effective useful lives in the scanner apparatus.

Still another advantage of the present invention is in providing a neat, uncluttered appearance for the many cables required to pass through the X-ray scanner apparatus gantry frame to operative communication with the radiation source and detector.

Other advantages and benefits will become apparent to those skilled in the art upon a reading and understanding of the specification.

BRIEF DESCRIPTION OF THE DRAWINGS

The invention may take physical form in certain parts and arrangements of parts, a preferred embodiment of which will be described in detail in the specification and illustrated in the accompanying drawings which form a part hereof and wherein:

FIG. 1 is a perspective and general view of an X-ray scanner apparatus to which the subject invention is deemed particularly applicable;

FIG. 3 is a cross-sectional view taken along lines 3—3 of FIG. 2;

FIG. 7 is a view showing a portion of the tension means roller chain in partial cross-section;

DESCRIPTION OF THE PREFERRED EMBODIMENT

Figure 2:
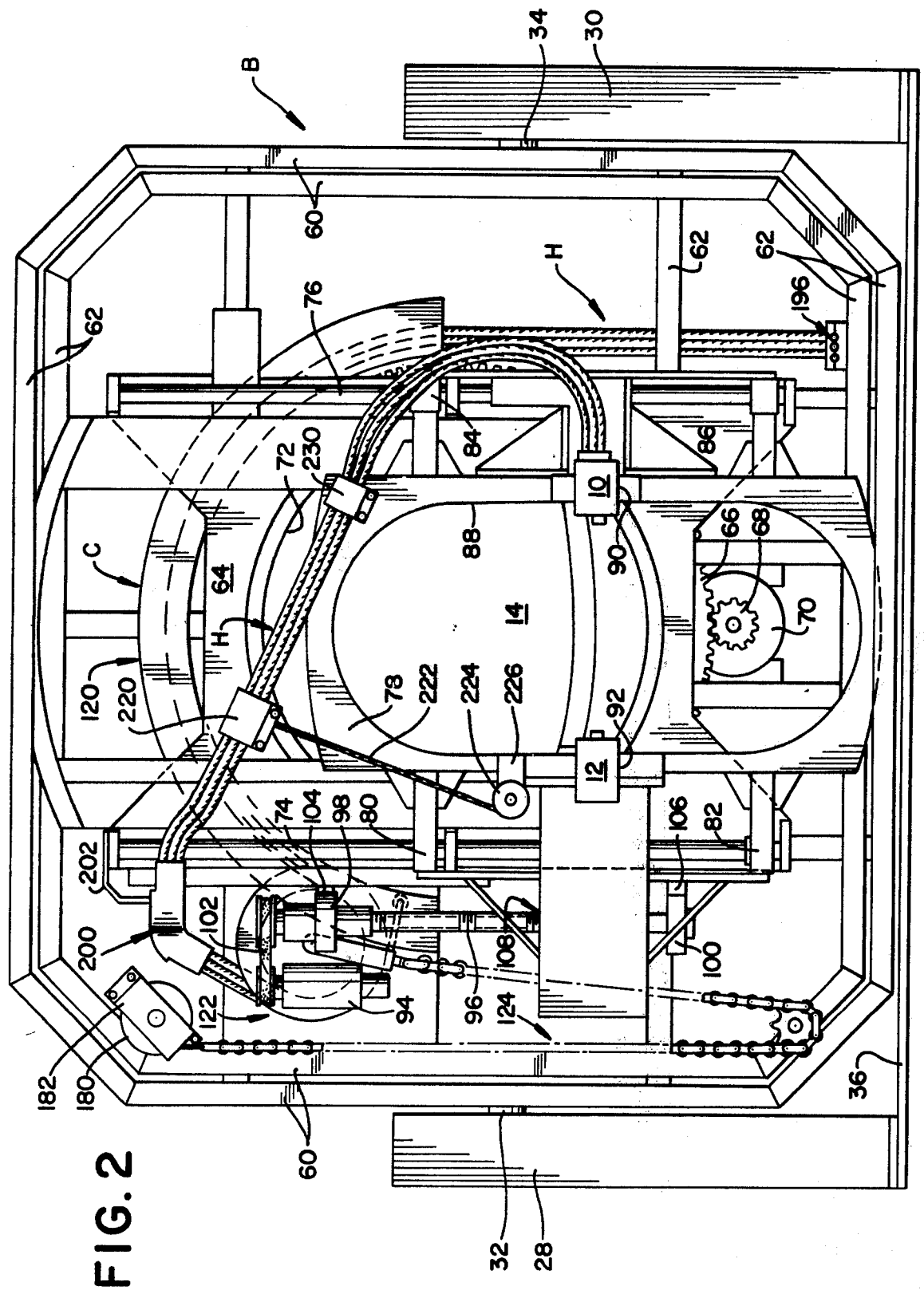
FIG. 2 is a front elevational view of a gantry frame for the X-ray scanner apparatus shown in FIG. 1 and showing incorporation of the subject invention therein.

Referring now to the drawings wherein the showings are for purposes of illustrating the preferred embodiment of the invention only and not for purposes of limiting same, the FIGURES show an X-ray scanner apparatus A which has therein a gantry frame B and a cable control and take-up mechanism C which comprises the present invention. Mechanism C is employed in conjunction with and for controlling the cables of a cable harness H.

With reference to FIG. 1, X-ray scanner A houses the X-ray scanner itself which includes a radiation source 10 which transmits radiation, usually X or gamma radiation, to a detector 12 with components 10, 12 disposed on opposite sides of an opening 14 in which the patient or medium of the radiation would lie. The radiation source 10 and detector 12 are mounted for linear traverse and rotational movement in a manner to be more particularly described hereinafter. Generally, however, the source of radiation and detector, along with appropriate circuitry and gantry frame B, are mounted for traverse and rotational movement in a casing 16 having a front face 18, a rear face 20, opposed sides 22, 24 and a top 26. Mounted outwardly from and adjacent sides 22, 24 of casing 16 are vertical supports 28, 30, respectively, which support the casing on pivot mountings 32, 34 (FIG. 2) which facilitate some limited rotation of the scanner apparatus therearound. A base 36 extends between and is connected to vertical supports 28, 30.

A patient table generally designated 40 is disposed adjacent front face 18 of casing 16 at opening 14. The patient table is comprised of a table portion 42 which is mounted on a base 44.

The specifics of operation for the X-ray scanner apparatus disclosed above does not form a specific part of the present invention. The overall concepts involved in such apparatus may, however, be obtained from the Hounsfield-3,778,614 U.S. Patent which is incorporated herein by reference and which are also disclosed in the commonly assigned pending application, Ser. No. 691,313, filed June 1, 1976.

With particular reference to FIG. 2, casing 16 covers gantry frame B which is generally comprised of vertical gantry members 60 and horizontal gantry frame members 62. The specifics of construction of this frame do not form a part of this invention and only some of these members are generally shown in order that those skilled in the art may appreciate the preferred environment of the subject invention. Disposed in the gantry frame is a rotate frame generally designated 64 which is generally planar in nature, generally vertically disposed and mounted for selective rotational movement in the plane of the gantry frame by conventional means not shown. Rigidly affixed to the rotate frame is a large circular drive gear 66 having drive teeth disposed along the outer peripheral edge thereof. A pinion gear 68 engages this drive gear and is operably mounted to a drive motor generally designated 70 rigidly mounted to gantry frame B. Energization of drive motor 70 to rotatably drive pinion gear 68 in one direction or another will affect opposite rotational movement of rotate frame 64 through drive gear 66. Rotate frame 64 includes an enlarged generally centrally located circular opening 72 which acts to define a portion of opening 14 through the X-ray scanner apparatus. Conveniently mounted so as to extend along and adjacent the outer side edges of rotate frame 64 are a pair of elongated slide bars or rods generally designated 74, 76.

A traverse frame generally designated 78 having a planar configuration is closely associated with and in operative communication with rotate frame 64. This traverse frame includes mounting arms 80, 82, 84 and 86 extending outwardly from the opposed side edges thereof. Mounting arms 80, 82 are slidably received on elongated slide bar 74 and mounting arms 84, 86 are slidably received on elongated slide bar 76. With this configuration, traverse frame 80 is movable longitudinally along or across rotate frame 64 for reasons and purposes to be described in detail hereinafter. Traverse frame 78 includes an elongated, generally centrally located opening 88 therethrough which also defines a portion of opening 14 through the scanning apparatus. Generally centrally mounted along the opposed side edges of traverse table 78 are radiation source 10 at area 90 and detector 12 at area 92.

A drive motor generally designated 94 is operably connected to an elongated threaded drive shaft or screw 96 extending between journals 98, 100 by a drive belt 102. This drive motor with journal 98 and journal 100 are conveniently affixed to rotate frame 64 by mounting brackets 104, 106, respectively. Drive shaft 96 is operably mounted to traverse frame 78 by a drive nut arrangement conveniently located as at area 108. With this arrangement and when drive motor 94 is energized to drive threaded shaft 96 in one direction or the other through drive belt 102, the drive shaft, through the drive nut, will cause traverse frame 78 to be moved on rotate frame 64 along elongated slide bars 74, 76 in one direction or the other.

In operation of the scanner, it is desired to variously move radiation source 10 and detector 12 around opening 14 in order that the necessary and/or desirable X-rays may be taken. For this purpose, there is typically a first or normal position for the radiation source and detector within the scanner apparatus itself and such a position for these components is shown in FIG. 2. From this first or normal position, the radiation source and detector may be moved to a number of different or second positions by simply moving rotate and traverse frames 64, 78 independently or in conjunction with each other through drive motors 70, 94, respectively. More particularly, the rotate frame allows the radiation source and detector to be rotated generally around the axis of opening 14 and the traverse frame allows the radiation source and detector to be moved transversely across the plane of opening 14. Traverse frame 78 always rotates with rotate frame 64 since it is mounted thereto but it may also independently traverse the rotate frame through use of drive motor 94.

The specifics of construction for gantry frame B, rotate frame 64 and traverse frame 78 have not been shown in precise detail since they do not form a part of the present invention. Rather, they have been shown somewhat schematically in order that those skilled in the art may appreciate the primary focus and preferred environment for the present invention which will be described in detail hereinafter.

Because of the complexity of the overall X-ray scanner construction, the complexity of the attendant and supportive equipment, and the nature of radiation source 10 and detector 12, a number of flexible cables which comprise a cable harness generally designated H in FIG. 2 must be passed through the gantry frame for purposes of rendering the radiation source and detector operative. Since these components are movable within the gantry frame between first and second positions, it is also necessary that a certain amount of slack be provided for these cables in order that they will not be torn from their operative connections with their associated components. Moreover, it is also necessary to locate the cables within the gantry frame so that during operation of the scanning apparatus and movement of the radiation source and detector, the cables will not rub against or be trapped in the scanning apparatus which could otherwise cause wearing and/or damage thereto.

Therefore, and in accordance with the present invention, the cable control and take-up mechanism generally designated C in FIG. 2 is provided. In FIG. 2, this mechanism is shown as comprising three major components, that is, a cable track or trough generally designated 120, a cable wheel assembly generally designated 122 and a biasing or tensioning means generally designated 124. While the general configuration and placement of this mechanism is generally shown in FIG. 2, specific description thereof will hereinafter primarily be made with reference to FIGS. 4–8.

Figure 4:
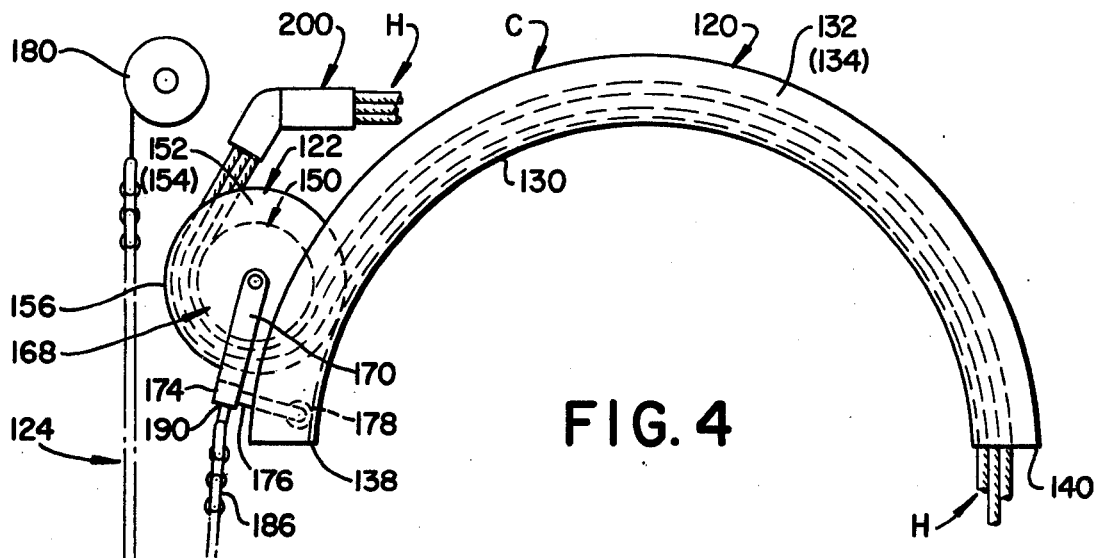
FIG. 4 is a view of the subject cable control and take-up mechanism in and of itself with the cable wheel assembly in the home position.
Figure 5:
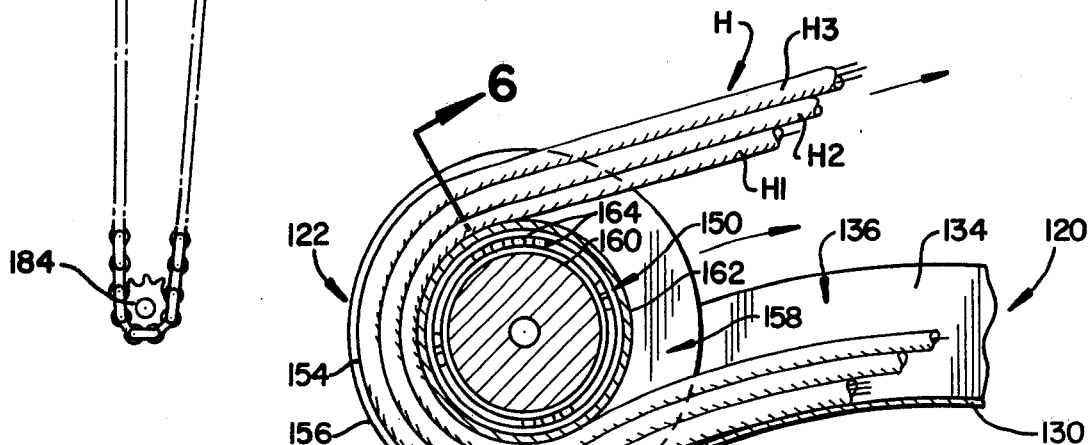
FIG. 5 is an enlarged view showing the cable wheel assembly with one side wall of the cable trough and one side of the cable wheel assembly removed for ease of illustration.
Figure 6:
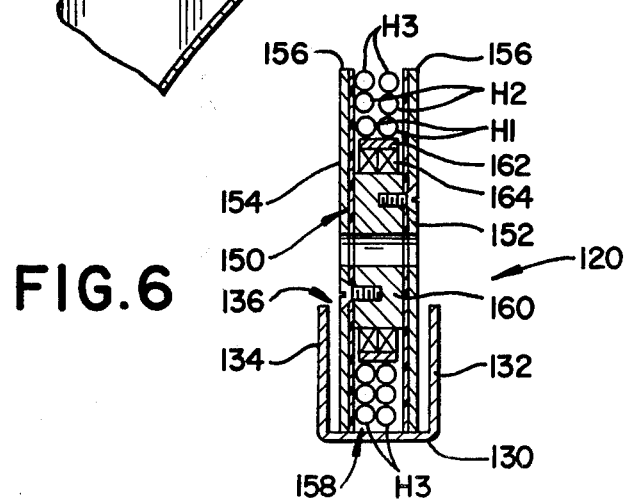
FIG. 6 is a cross-sectional view taken along lines 6—6 of FIG. 5.

Referring to FIGS. 4–6, cable track or trough 120 is shown as having a bottom wall 130 and spaced apart side walls 132, 134 upstanding therefrom so as to define a trough area 136 therebetween. The cable trough has an arcuate configuration which is generally semi-circular extending between a first end 138 and a second end 140. Trough 120 is rigidly affixed by convenient means to gantry frame B so that ends 138, 140 are disposed slightly above the horizontal centerline of opening 72 in rotate frame 64 and generally arcuately coextensive with drive gear 66 as best shown in FIG. 2. Moreover, cable trough 120 is mounted to gantry frame B to the rear of rotate frame 64 as viewed in FIG. 2. While trough 120 has been specifically described with reference to a U-shaped trough, it would also be possible to use other trough or track-like constructions without departing from the intent or scope of the present invention.

With continued reference to FIGS. 4–6, cable wheel assembly generally designated 122 is comprised of a cylindrical hub area 150 and a pair of spaced apart circular side discs 152,154 having outer peripheral edges 156 in rolling engagement with bottom wall 130 of the cable trough. The hub area and side discs define a cable channel area 158 therebetween. Hub area 150 itself is comprised of concentric inner and outer cylindrical hubs 160,162 having bearing members 164 disposed therebetween in order that relative rotational movement may be advantageously obtained between the two hubs for reasons which will become apparent hereinafter. Side discs 152,154 are conveniently mounted to inner hub 160 by bolts or the like generally designated 166 in order that the side discs may be rotated with the inner hub, independently of outer hub 162. Moreover, and for reasons which will become apparent hereinafter, inner or facing surfaces of side discs 152,154 are coated with polytetrafluoroethylene in order to provide good sliding surfaces.

Pivotally affixed to the axis or center of cable wheel assembly 122 is a biasing or tensioning means connecting bracket generally designated 168. This bracket is comprised of a yoke-like arrangement having opposed sides 170 extending radially outward from the cable wheel assembly axis and connected together outwardly of side disc peripheral edges 156 of an end member 174. Extending outwardly of this end member toward bottom wall 130 of cable trough 120 is a leg 176 having a roller 178 affixed to the outermost end thereof which is in rolling engagement with bottom wall 130. The length of leg 176 is such that mounting bracket 178 will be retained slightly above the upper edges of cable trough side walls 132,134 in order to prevent the tensioning means from rubbing thereagainst or catching thereon.

Biasing or tensioning means 124 is comprised of a conventional spring reel arrangement 180 rotatably mounted to gantry frame B as by mounting bracket 182 (FIG. 2) adjacent the upper portion of the frame. An idler sprocket 184 is rotatably mounted to the frame adjacent the lowermost portion thereof. A double pitch roller chain 186 utilizing oversized plastic rollers 188 therein (FIG. 8) extends from spring reel 180, around idler sprocket 184 to outer end 174 of mounting bracket 168 and is affixed thereto as at 190. Because of the length of chain 186, a pair of spring reels 180 may have to be employed to accomplish the concepts contemplated for the subject invention. Further, the plastic material preferred for oversized rollers 188 is made from acetal resins.

Harness H is comprised of cable rows H1, H2 and H3 and enters X-ray scanner A through rear face 20 adjacent the lower right hand portion thereof as viewed in FIG. 2 where it is clamped in position by conventional clamp means 196. The harness is then strung through gantry frame B to second end 140 of cable trough 120, then along and in the trough toward first end 138 thereof, around a portion of the cable wheel assembly in cable channel area 158 and then generally back toward trough second end 140.

As best shown in FIG. 6, cable rows or layers H1, H2 and H3 comprise three separate rows or layers each having two cables therein. The width of trough area 136 is slightly greater than the maximum width of any of these three rows and side discs 152,154 are also spaced apart from each other slightly greater than the maximum width of any one of the cable rows or layers but less than the width of trough area 136 in order that the cable wheel assembly may be received in the trough. Moreover, the radial distance between outer hub 162 and peripheral edges 156 of side discs 152,154 is slightly greater than the combined height of the three rows of cables H1, H2 and H3 in order that edges 156 may be in rolling engagement with trough bottom wall 130.

From the cable wheel assembly, the cables of harness H are passed to an "S" shaped cable bracket generally designated 200 which is rigidly affixed to rotate frame 64. As best shown in FIG. 3, cable bracket 200 is mounted to rotate frame 64 by means of a mounting bracket 202 and has a lead in end 204, a central portion 206 and an exit end 208. As noted hereinabove, control and take-up mechanism C is mounted behind rotate frame 64 and traverse frame 78 with radiation source 10 and detector 12 are disposed to the front of the rotate frame as viewed in FIG. 2. It is therefore necessary to string the cables of harness H from the rear of the rotate frame to the front thereof in order that they may be connected to radiation source 10 and detector 12. This change in direction or disposition of harness H occurs as the harness is passed into lead in end 204, then through central portion 206 and outwardly of exit end 208 where central portion 206 is disposed generally transverse to the plane of rotate frame 64. Moreover, the cables of harness H are tightly retained in cable bracket 200 so that during apparatus operation, the cables may not slip therethrough in one direction or the other. Furthermore, and as best shown in FIGS. 2 and 4, bracket 200 receives and locates the cable harness so that it extends around the wheel assembly hub area 150 over approximately 180° of the circumference thereof.

After passing outwardly of exit end 208, the cables are passed toward terminal end connections (not shown) with the operative components which they are to supply or control. Disposed intermediate exit end 208 of cable bracket 200 and these terminal connections is a tensional cable bracket 220. Bracket 220 is closely received over the cables of harness H and has a chain or cable 220 extending therefrom to a spring reel 224 which, in turn, is mounted by a reel bracket 226 to traverse frame 78. Intermediate cable bracket 200 and the terminal end connections of harness H is another cable mounting bracket generally designated 230 which is mounted directly to traverse frame 78.

As particularly noted in FIGS. 2 and 4, and with rotate frame 64 and traverse frame 78 in the normal or first position shown therein, wheel assembly 122 itself is in a home position in cable trough 120 adjacent first end 138. Biasing or tensioning means 124 exerts a biasing pressure through chain 186 against the cable wheel assembly in order to continuously urge it to that home position. In scanner apparatus operation and if only traverse frame 78 is moved relative to the apparatus and rotate frame 64 on the elongated slide bars or rods 74,76, cable wheel assembly 122 will remain in the home position as shown in FIGS. 2 and 4. This, of course, is because the cable is closely retainingly received in bracket 220 and the bracket itself is mounted to the rotate frame. As the traverse frame is moved relative to the rotate frame by drive motor 94, cable bracket 220 through spring reel 224 and chain or cable 222 retains a slight tension on the cable so that it will not flop or be otherwise misaligned between the two frames which could cause cable damage or the like and generally guides the harness across the front of the traverse frame as that frame nears an extended position adjacent the extremities of slide bars 74,76.

Figure 8:
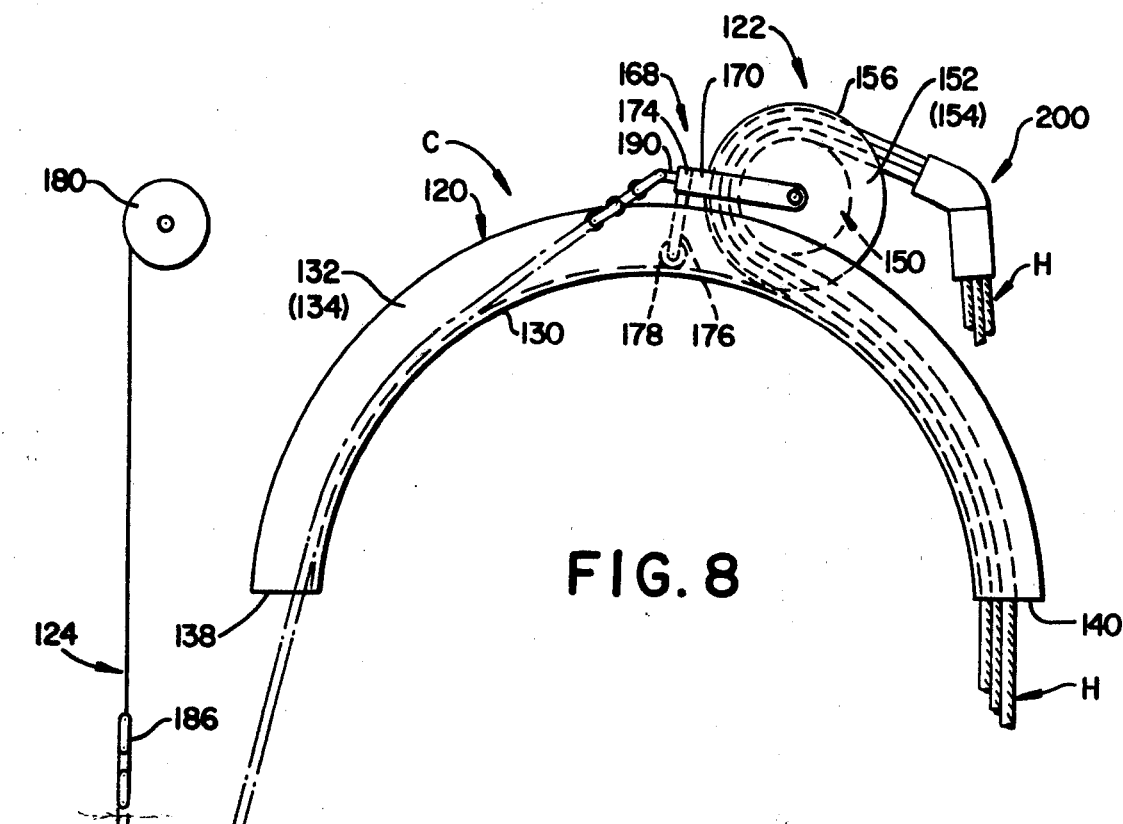
FIG. 8 is a view of the subject cable control and take-up mechanism with the cable wheel assembly moved to its extended position in response to movement of the radiation source and detector; and, FIG. 9 is a cross-sectional view similar to FIG. 6 showing a slightly modified configuration of the cable trough and cable wheel assembly.

When rotate frame 64 is moved in a clockwise direction from the position shown in FIG. 2, cable bracket 200 which is affixed to the rotate frame is also rotated so as to pull cable wheel assembly 122 along cable trough 120 from the home position shown in FIG. 4 to an extended position spaced therefrom along trough 120 such as that shown in FIG. 8. It is cable bracket 200 which pulls the cables in the direction of rotation thereby also pulling the cable wheel assembly along the cable trough. As the cable wheel assembly is moved from the home position shown in FIGS. 2 and 4 to the extended position shown in FIG. 8, cable bracket 200 pulls the cables of harness H in the same direction as the direction of the bracket of rotation. In this process, the cables peel themselves from trough bottom wall 130 and roll over outer hub 162 of cable wheel assembly 122 in order to follow movement of bracket 200. It should be here noted that all the cables in layers H1, H2 and H3 of the harness which are positioned in cable trough 120 remain stationary and do not slide through the trough. It should also be noted that bracket 200 maintains the cables in contact with outer hub 162 over generally 180° of the circumference thereof regardless of whether the cable wheel assembly is in the home position of FIGS. 2 and 4 or the extended position of FIG. 8. Of course, during rotation of rotate frame 64 through a specific degree or amount of angular travel, the cable wheel assembly only moves one-half of that degree or amount of angular travel.

The design of the cable wheel assembly to provide independent rotational movement between inner and outer cylindrical hubs 160,162 and the mounting of side discs 152,154 to the inner hub allows the cable wheel assembly to roll at the required speed on trough bottom wall 130 but its angular velocity is not necessarily the angular velocity of each of the cable layers H1, H2 and H3. Each of the layers can have its own angular and tangential velocity with only minute sliding occurring between the cable layers during a flexing motion, that is, movement between the home and extended positions. In order to minimize the friction between each layer, a light application of silicone spray may be given to the cables and to the cable wheel assembly.

Biasing or tensioning means 124 maintains the cable wheel assembly and harness under a constant tension in order to prevent the cables from sliding in the cable trough. Actually, the biasing or tensioning means merely provides a balancing pull-back force to the cable wheel assembly. Spring reel 180 may be pretorqued in order to provide an adequate and desired balancing force even when the cable wheel assembly and cables are in or between the 12 and 3 o'clock position as viewed in FIGS. 2, 4 and 8. The oversized rollers 188 used in roller chain 186 provide rolling, rather than sliding friction on trough bottom wall 130 when the cable wheel assembly is moved between the home and extended position where engagement between the chain and trough is shown in FIG. 8. Moreover, the construction of the rollers from plastic is deemed to enhance this rolling and both features act to eliminate undesirable wear and drag on the overall control and take-up mechanism operation. Of course, movement of cable wheel assembly 122 may be to positions other than that specifically shown in FIG. 8, and these positions are dictated solely by the tension exerted on harness H through cable mounting bracket 200 as the bracket is rotationally moved clockwise as viewed in the FIGURES with rotate frame 64.

Normally, rotate frame 64 is only moveable through approximately 180° degrees of rotation by drive gear 66 and drive motor 70. When the rotate frame is moved to its maximum rotated position, the cable wheel assembly is moved to its furthest extended position along the cable trough. When the rotate frame is moved from a second position, counterclockwise in the view of the FIGURES back to the first position, harness H is laid back into the cable trough from around the cable wheel assembly as the cable wheel assembly itself is moved from an extended position back to the home position in response to movement of cable bracket 200 with the rotate frame and at the urging of biasing or tensioning means 124.

Figure 9:
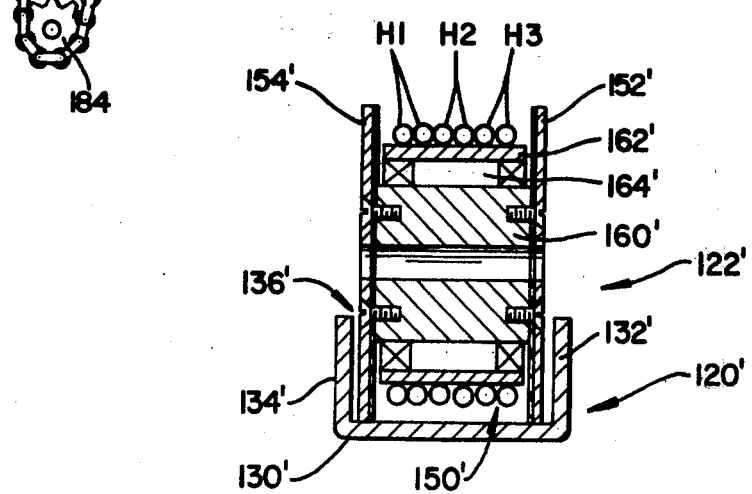

FIG. 9 shows a slightly modified form for locating the plurality of cables which comprise the cable harness in and between the cable trough area and the wheel assembly channel area. For ease of illustration and appreciation of this modification, like components are identified by like numerals with a primed (') suffix and new components have new numerals. Accordingly, bottom wall 130' of cable trough 120' has been widened somewhat in order that all six cables H1', H2' and H3' of the cable harness may be received longitudinally therealong in a side by side relationship. In addition, the width of cable wheel assembly 122 has been correspondingly increased so that all of the individual cables may be received in a side by side relationship over hub area 150'. This particular structural modification is such that any difficulties encounered with varying angular and tangential velocities between adjacent rows of cables and the minute sliding between layers during flexing or movement of the cables around the cable wheel assembly hub area 150' may be eliminated.

The subject cable control and take-up mechanism has been specifically described with reference to an X-ray scanner mechanism wherein a radiation source and detector may be variously rotated or traversed in order to achieve particular desired end X-raying results. However, it will be apparent to those skilled in the art that the invention has broader applications and may be used in other apparatus and environments where a single flexible cable or the like, a plurality of flexible cables or the like or a flexible cable harness or the like are connected to at least one operating member which may be moved from a first position to one or more second positions in an operating plane. The invention is particularly applicable to those instances where careful control and take-up of a flexible cable or the like is important to prevent cable damage or eliminate undesired excessive premature cable wear during apparatus operation.

The invention has been described with reference to the preferred embodiment. Obviously, modifications and alterations will occur to others upon a reading and understanding of this specification. It is our intention to include all such modifications and alterations insofar as they come within the scope of the appended claims or the equivalents thereof.

Having thus described our invention, we now claim:

1. A cable control and take-up mechanism for a plurality of elongated flexible cables and the like stationarily mounted at a first area to an X-ray scanning apparatus and operably connected at a second area to a radiation source and detector which selectively movable relative to said apparatus in a predetermined path between a first position and a second position spaced from said first position, said control and take-up mechanism comprising:

a cable track fixedly mounted to said apparatus and having first and second spaced apart ends, a portion of said plurality of cables extending between said first and second areas passing in a side by side relationship longitudinally along at least a portion of said track;

a cable wheel assembly communicating with said track and adapted for selective movement relative thereto, said cable wheel assembly including a cylindrical hub having an outer surface and spaced apart sides extending radially outward from the ends of said hub with the area between said sides and hub outer surface defining a cable receiving channel wherein portions of said plurality of cables are received in said channel and around said hub in a side by side relationship between said track and said second area, said cable wheel assembly being selectively movable relative to said track between a home position adjacent said track first end and an extended position spaced along said track toward said track second end in response to the tension force of at least one of said plurality of cables as said radiation source and detector are moved from said first toward said second position; and, means for continuously urging said cable wheel assembly toward said home position against the tension of said at least one cable.

2. The mechanism as defined in claim 1 wherein said cable track has an arcuate configuration longitudinally thereover between said first and second ends.

3. The mechanism as defined in claim 2 wherein said cable track has a generally semi-circular configuration over the length thereof.

4. The mechanism as defined in claim 2 wherein said cable track is defined by an elongated trough having a bottom wall and spaced apart side walls upstanding therefrom.

5. The mechanism as defined in claim 1 wherein said cable wheel assembly has an assembly axis and said sides are rotatable about said assembly axis independently of said hub.

6. The mechanism as defined in claim 5 wherein said hub is comprised of concentric inner and outer cylindrical hubs mounted for independent rotation about said assembly axis, said assembly sides being affixed to said inner hub to facilitate relative rotational movement between said outer hub and said sides.

7. The mechanism as defined in claim 5 wherein the facing surfaces of said wheel assembly sides are coated with polytetrafluoroethylene.

8. The mechanism as defined in claim 1 wherein said means for continuously urging comprises a spring biased reel spaced remote from said cable wheel assembly and operably connected thereto by an elongated flexible member, said reel being spring biased in a manner such that said cable wheel assembly will be continuously urged to said home position with said elongated flexible member being paid out from said reel as said wheel assembly is moved from said home to said extended position and paid onto said reel as said assembly is moved from extended to said home position.

9. The mechanism as defined in claim 1 wherein said plurality of cables are maintained in contact with said wheel assembly hub generally over the same degree of the circumference thereof when said assembly is in said home position and as said assembly is moved between said home and extended positions.

10. The mechanism as defined in claim 1 wherein said first and second positions of said radiation source and detector are coplanar and disposed in an operating plane, movement of said cable wheel assembly relative to said track between said home and extended positions being in a plane generally parallel to said operating plane.

11. In X-ray scanning apparatus of the type having a radation source and detector mounted therein for selective movement at least rotationally through an operating plane between first and second positions around an apparatus opening and wherein a plurality of elongated cables extend through said apparatus from a first area to operating engagement with at least said radiation source at a second area, the improvement comprising:

a cable control and take-up mechanism for said plurality of cables, said mechanism including a cable track fixedly mounted to said apparatus and having first and second spaced apart ends, a portion of said plurality of cables extending between said first and second areas passing in a side by side relationship longitudinally along at least a portion of said track; a cable wheel assembly communicating with said track and adapted for selective movement relative thereto, a portion of said plurality of cables being received around said wheel assembly in a side by side relationship between said track and said second area, said cable wheel assembly being selectively movable relative to said track between a home position adjacent said track first end and an extended position spaced along said track toward said track second end, said cable wheel assembly being movable between said home and extended positions in response to the tension of at least one of said cables as said radiation source and detector are movable between said first and second positions; and, means for continuously urging said cable wheel assembly toward said home position against the tension of said at least one cable.

12. The improvement as defined in claim 11 wherein said cable track has an arcuate configuration longitudinally thereover between said first and second ends.

13. The improvement as defined in claim 12 wherein said cable track is defined by an elongated trough having a bottom wall and spaced apart side walls upstanding therefrom.

14. The improvement as defined in claim 11 wherein said cable wheel assembly includes a cylindrical hub having an outer surface and spaced apart sides extending radially outward from the ends of said hub with the area between said sides and hub outer surface defining a cable receiving channel with the portion of said plurality of cables received over said cable wheel assembly received in said channel and around said hub.

15. The improvement as defined in claim 14 wherein said cable wheel assembly has an assembly axis and said sides are rotatable about said assembly axis independently of said hub.

16. The improvement as defined in claim 15 wherein said wheel assembly sides are generally circular and have outer peripheral edges disposed in rolling engagement with said track, the transverse distance between said track and wheel assembly hub being slightly greater than the greatest transverse height of said plurality of cables extending upwardly from said track.

17. The improvement as defined in claim 15 further including a cable retaining member disposed between said cable wheel assembly and said radiation source, said retaining member being mounted in said apparatus for selective movement with said radiation source and detector for maintaining said plurality of cables in a generally continuous contact with said wheel assembly hub over the same general degree of the circumference thereof as said radiation source and detector are moved between said first and second positions.

18. The improvement as defined in claim 17 wherein said radiation source and detector are operably mounted to a rotate frame in said scanner apparatus for providing said at least rotational movement therefor, said cable retaining member also being mounted to said rotate frame for at least rotational movement coextensive with said radiation source and detector.

19. The improvement as defined in claim 11 wherein said means for continuously urging comprises a spring biased reel spaced remote from said cable wheel assembly and operably connected thereto by an elongated flexible member, said reel being spring biased in a manner such that said cable wheel assembly will be continuously urged to said home position with said flexible member being paid out from said reel as said wheel assembly is moved from said home to said extended position and paid onto said reel as said assembly is moved from said extended to said home position.

20. A cable control and take-up mechanism for a plurality of elongated flexible cables and the like stationarily mounted at a first area to an X-ray scanner apparatus then extending to and operably connected at a second area to a radiation source and a detector which are selectively movable relative to said apparatus in a predetermined operating plane between a first normal position and a second position spaced from said first position, said control and take-up mechanism comprising:

an elongated arcuate cable track fixedly mounted to said apparatus in a plane generally parallel to said operating plane with said track having first and second spaced apart ends, a portion of said plurality of cables extending between said first and second areas in a side by side relationship longitudinally along at least a portion of said track;

a cable wheel assembly communicating with said cable track and adapted for selective rolling movement therein and having an assembly axis extending generally normal to the longitudinal axis of said track, said cable wheel assembly including a cylindrical hub having an outer surface and spaced apart sides extending radially outward of said hub with said sides and hub being rotatable about said assembly axis independently of each other, the area between said sides and hub defining a cable receiving channel with a portion of said plurality of cables being received in said channel in a side by side relationship in contact with a circumferential portion of said hub between said cable track and said second area, said cable wheel assembly being selectively rollingly movable on said track about said assembly axis between a home position adjacent said track first end when said radiation source and detector are in said first position and an extended position spaced along said track toward said track second end as said radiation source and detector are moved from said first toward said second position, said cable wheel assembly being moved from said home toward said extended position by the tension force exerted on said assembly around said hub by at least one of said plurality of cables as said radiation source and detector are moved from said first toward said second position; and, means for continuously urging said cable wheel assembly toward said home position against the tension force of said at least one cable.

21. The mechanism as defined in claim 20 wherein said plurality of cables are generally in contact with said cable wheel assembly hub over approximately 180° of the circumference thereof when said assembly is in said home position and as said assembly is moved between said home and extended positions.

22. The mechanism as defined in claim 21 wherein said hub is comprised of concentric cylindrical inner and outer hubs mounted for independent rotation about said assembly axis with said assembly sides being mounted to said inner hub to facilitate relative rotational movement between said outer hub and said sides, the outer peripheral edges of said sides being disposed in rolling engagement with the bottom wall of said trough.

23. The mechanism as defined in claim 22 wherein said track comprises a trough having a bottom wall and spaced apart side walls upstanding therefrom, said cable wheel assembly being disposed in rolling engagement with said bottom wall.

24. The mechanism as defined in claim 22 wherein the facing surfaces of said wheel assembly sides are coated with polytetrafluoroethylene.

25. The mechanism as defined in claim 20 wherein said means for continuously urging comprises a spring biased reel spaced remote from said cable wheel assembly and operably connected thereto by an elongated flexible member, said reel being spring biased in a manner such that said cable wheel assembly will be continuously urged to said home position with said elongated flexible member being paid out from said reel as said wheel assembly is moved from said home to said extended position and paid onto said reel as said wheel assembly is moved from said extended to said home position.

26. The mechanism as defined in claim 25 wherein said cable wheel assembly further includes a mounting yoke pivotally mounted to said wheel assembly at said assembly axis and extending radially outward therefrom beyond the outer peripheral edges of said wheel assembly sides, said flexible member comprising a length of roller chain with the rollers thereof constructed from a plastic material and wherein said chain is affixed to said mounting yoke at an area thereof spaced radially outward of said side peripheral edges, said cable wheel assembly also including means for maintaining said mounting yoke outer end at a desired spaced location from said track.

27. The mechanism as defined in claim 20 further including a cable retaining member disposed between said cable wheel assembly and said radiation source and detector, said retaining member being mounted in said apparatus for selective movement with said radiation source and detector for maintaining said plurality of cables in continuous contact with said wheel assembly hub generally over the same degree of the circumference thereof as said radiation source and detector are moved between said first and second positions.

* * * * *